US00PP36594P2

(12) United States Plant Patent
Hansen

(10) Patent No.: US PP36,594 P2
(45) Date of Patent: Apr. 8, 2025

(54) ***RUDBECKIA* PLANT NAMED 'Treasure Trove'**

(50) Latin Name: ***Rudbeckia* hybrid (L.)**
Varietal Denomination: Treasure Trove

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,342

(22) Filed: Nov. 22, 2024

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474
See application file for complete search history.

(56) References Cited

U.S. PATENT DOCUMENTS

PP28,498 P2 * 10/2017 Horvath ..... A01H 6/14
Plt./474

* cited by examiner

*Primary Examiner* — Susan McCormick Ewoldt

(57) ABSTRACT

The new and distinct hardy perennial plant, *Rudbeckia* 'Treasure Trove', has dense, rounded, mound habit with extensively-branched, predominately strong upright stems. Freely flowering habit beginning in early summer and continuing for about 6 to 7 weeks and repeating if deadheaded. Clean foliage shows significant resistance to Angular Leaf Spot and *Septoria* fungal leaf spot diseases. Inflorescences are in a capitulum with a single row of golden-yellow ray florets and central disk florets of greyed-purplish coloration. The new plant has a strong garden performance and is useful in the landscape en masse, as an accent, in containers or as cut flowers.

2 Drawing Sheets

Botanical denomination: *Rudbeckia* hybrid (L.).
Variety designation: 'Treasure Trove'.

STATEMENT REGARDING PRIOR DISCLOSURES UNDER 37 CFR 1.77(B)(6)

The first private offers for sale of the new plant were by Walters Gardens, Inc. on Nov. 27, 2023 and Nov. 28, 2023, to Centerton Nursery and Prides Corner, respectively. No plants of *Rudbeckia* 'Treasure Trove' have been sold in this country or anywhere in the world, nor has any disclosure of the new plant been made, more than one year prior to the filing date of this application, and such sale or disclosure would be a 35 U.S.C. § 102(b) exception.

BACKGROUND AND ORIGIN OF THE PLANT

The present invention relates to a new and distinct cultivar of *Rudbeckia* 'Treasure Trove'. The new plant was selected as a single seedling from the progeny of a cross by the inventor between the proprietary unnamed selection of *Rudbeckia fulgida* var. *deamii* (not patented) as the female or seed parent and the proprietary hybrid known only by the breeder code 15-1-10 (not patented) as the male or pollen parent in the summer of 2017 at a wholesale perennial nursery in Zeeland, Michigan. Seed was harvested in the fall of 2017 and eventually assigned the breeder code 17-10-1 toward the end of the trial period.

'Treasure Trove' was approved in a final evaluation in the summer of 2019 and slated for later introduction. The new plant was selected based on its habit, strong stems, ability to withstand lodging, disease resistance, attractive colorful foliage, high-quality flowers over a long period, and ability to attract pollinators. The new plant has been asexually first propagated in Zeeland, MI by division and later by shoot tip cuttings with the resultant asexually propagated plants remaining identical to the original plant, stable and true to type in successive generations.

SUMMARY OF THE INVENTION

Plants of the new Black-eyed Susan have not been observed under all possible combinations of environmental conditions and cultural practices. The phenotype may vary somewhat with variations in environmental conditions comprising temperature, daylength, light intensity, and fertility, without, however, any variations in genotype.

The following traits have been repeatedly observed and are determined to be the unique characteristics of the new *Rudbeckia* plant. These characteristics in combination distinguish 'Treasure Trove' as a new and distinct *Rudbeckia* plant:

1. Clean foliage shows significant resistance to Angular Leaf Spot and *Septoria* fungal leaf spot diseases;
2. Dense rounded mound plant habit with extensive branching habit and high number of inflorescences per stem;
3. Freely flowering habit beginning in early summer and continuing for about six to seven weeks, repeating if deadheaded;
4. Large inflorescences with a single row of golden-yellow ray florets and greyed-purplish disk florets;
5. Strong garden performance.

The female parent has a taller, broader, more open habit and larger foliage. The male parent has a taller habit than the new plant and the ray florets droop more.

The following cultivars are the most similar cultivars known to the inventor: 'American Gold Rush' U.S. Plant Pat. No. 28,498, 'Glitters Like Gold' U.S. Plant Pat. No. 30,933, and 'Goldsturm' (not patented).

'American Gold Rush' has a shorter more compact habit, less branching stems, the foliage is longer and narrower, with fewer inflorescences per stem, and slightly smaller flowers. 'Glitters Like Gold' has a slightly shorter habit with ray florets that are more yellowish gold and less orangish-yellow. 'Goldstrum' has a similar habit but is highly susceptible to *Septoria rudbeckiae*.

BRIEF DESCRIPTION OF THE DRAWINGS

The photographs of the new plant demonstrate the unique traits of *Rudbeckia* 'Treasure Trove' and the overall appearance of a three-year-old plant in the full sun display garden of a nursery in Zeeland, Michigan. The colors are as accurate as reasonably possible with color reproductions. Variation in ambient light spectrum, source and direction may cause the appearance of minor variation in color.

DETAILED BOTANICAL DESCRIPTION

Figure 1:
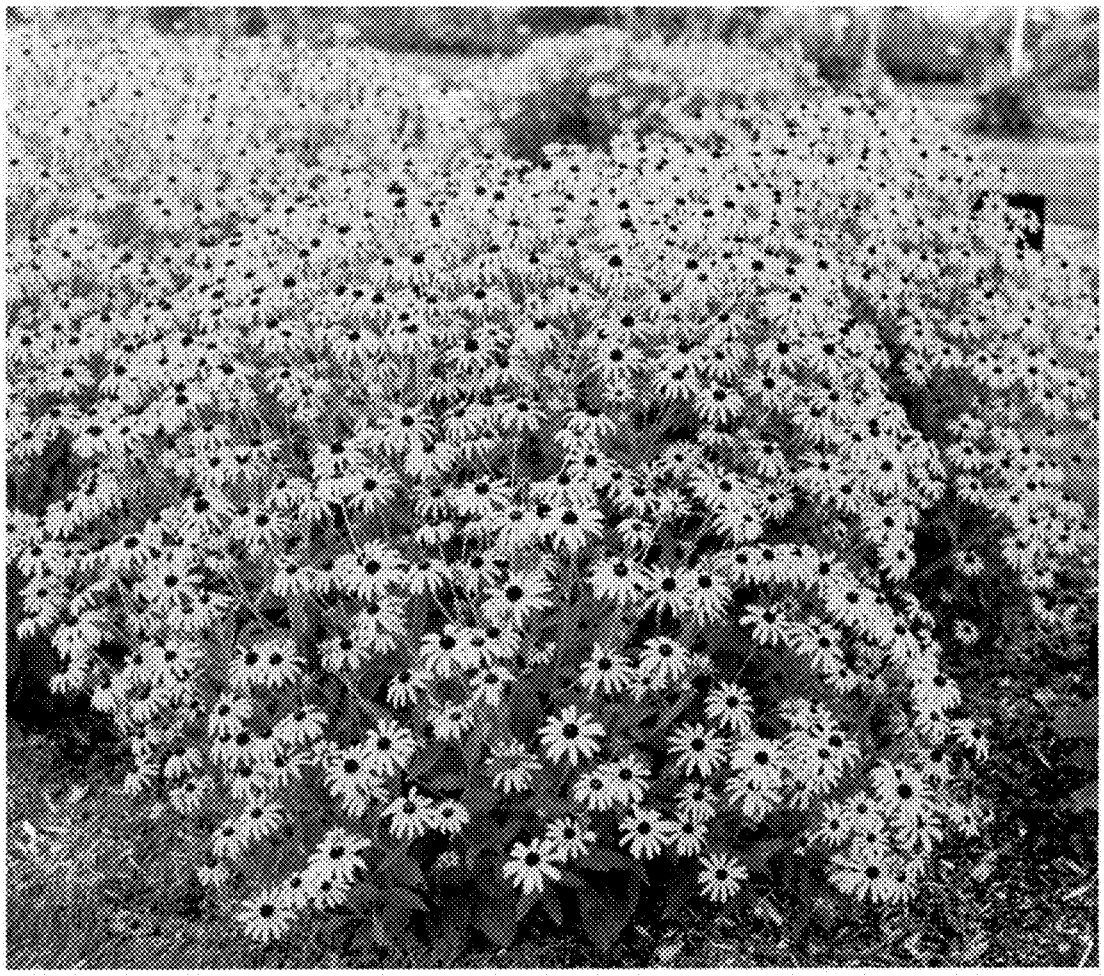
FIG. 1 shows the landscape habit of the new plant in flower.
Figure 2:
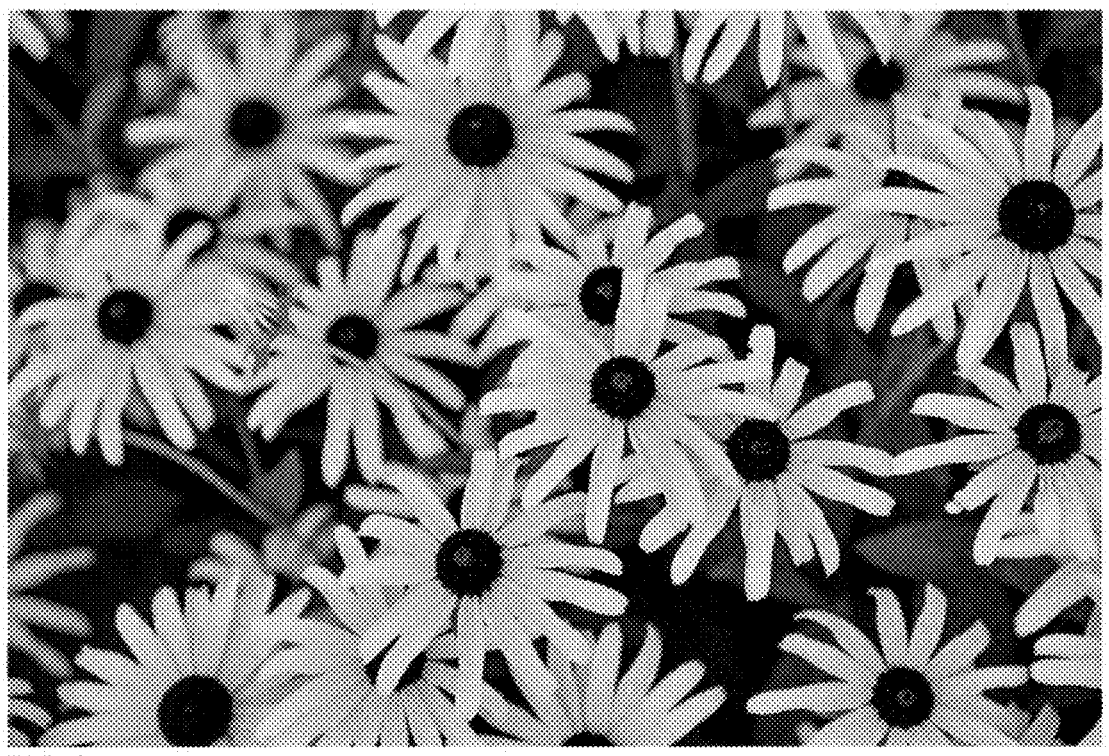
FIG. 2 shows a close-up of some inflorescences and bud.
Figure 3:
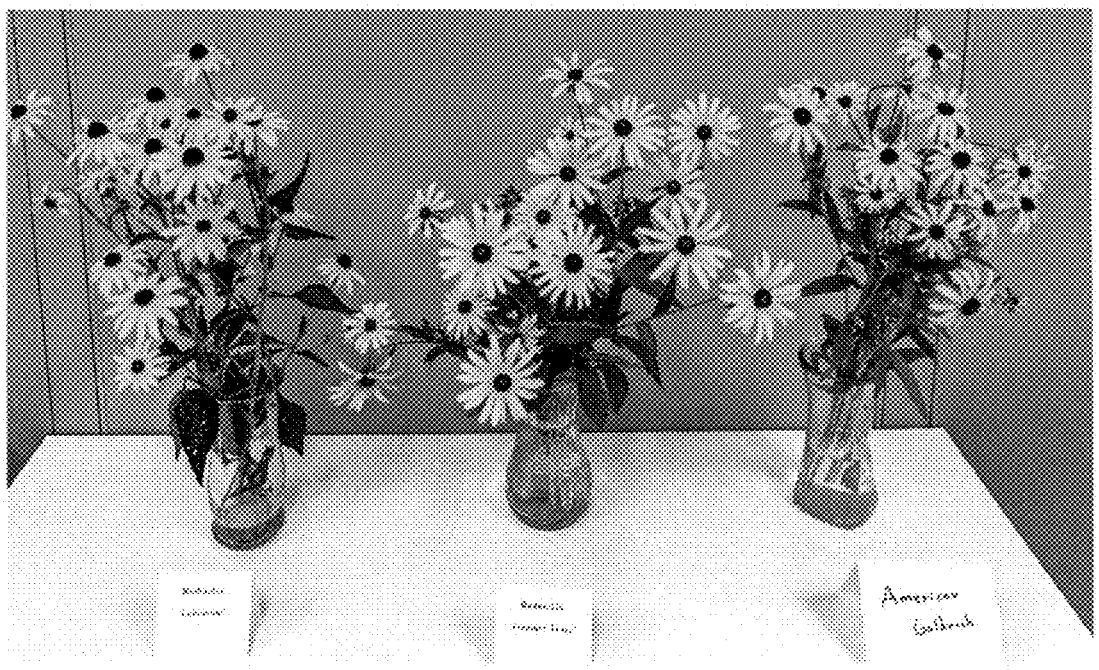
FIG. 3 shows a comparison of the new plant in the middle with 'Goldstrum' on the left and 'American Gold Rush' on the right.

The following descriptions and color references are based on the 2015 edition of The Royal Horticultural Society Colour Chart except where common dictionary terms are used. *Rudbeckia* 'Treasure Trove' has not been observed under all possible environments. The phenotype may vary slightly with different growing environments such as temperature, light, fertility, soil pH, moisture, and maturity levels, but without any change in the genotype. The following observations and size descriptions are based on three-year-old plants grown in a trial garden at a nursery in Zeeland, Michigan with supplemental fertilizer and water as needed and without growth regulators or pinching.

Botanical classification: *Rudbeckia* hybrid;

Parentage: The female (seed) parent is a proprietary unnamed selection of *Rudbeckia fulgida* var. *deamii*; the male (pollen) parent is 15-1-10;

Plant habit: Multi-stemmed, heavily-branched, herbaceous perennial forming a dense rounded mound;

Propagation: Stem cuttings and shoot tip tissue culture;

Plant size: To about 95 cm tall and 106 cm wide;

Time to initiate roots: About two weeks;

Growth rate: Vigorous; about 30 weeks to flower and finish in a 3.8-liter container from a rooted 25 mm plug liner;

Root description: Fibrous; medium thickness; light tan to white in color, depending on soil composition, water quality, fertilizer type and formulation, substrate temperature, and physiological age of roots; medium density;

Stems: About 56 per plant; cylindrical; hirsute to hispid with hairs to about 2 mm long; to about 56 cm long and 9 mm diameter at base; heavily branched;

Branches: About 12 primary branches per main stem beginning about 21 cm above soil; cylindrical; hirsute; strong; flexible; to about 30 cm long to peduncle and 4 mm diameter at base;

Branch aspect: About 30-degree to 45-degree angle away from main stem;

Nodes: About 5 below lowest branch; average internode length about 5 cm; node color nearest RHS 146A;

Stem and branch color: Proximally nearest RHS 146C, distally RHS 146A and RHS 138A with portions exposed to high light blushed strongly with nearest RHS N186C;

Leaf description: Ovate; alternate; apex acute; base attenuate; margin crenate with about 7 per side; scaberulose and hirsutulous adaxial and abaxial;

Leaf size: Basal leaves to about 14 cm long and 10 cm wide, average about 10 cm long and 7.5 cm wide; decreasing distally on caudal leaves;

Leaf color: Young adaxial nearest RHS NN137B, young abaxial nearest RHS 146A; mature flowering stage adaxial nearest RHS NN137A, and abaxial nearest RHS 147B;

Veins: Reticulate; slightly recessed and glabrous adaxial, abaxial costate; micro-hirsutulous adaxial and abaxial;

Vein color: Young adaxial midrib and primary proximal veins nearest RHS 145A and secondary distal veins abaxial between RHS 146D and RHS 145A, young abaxial midrib and primary proximal veins nearest RHS 146D and secondary distal veins nearest RHS 146A; mature adaxial midrib nearest RHS 146C and primary and secondary veins nearest RHS 146B and secondary veins nearest RHS 137B, mature abaxial midrib and primary veins between RHS 146C and RHS 147C and secondary veins between RHS 137A and RHS 137B;

Petioles: On basal leaves proximal portion concavo-convex and distal adaxial portion applanate; hirsutulous adaxial and abaxial; to about 17 mm long, 8 mm across at base and 3 mm across in middle; decreasing distally on caudal leaves;

Petiole color: Adaxial and abaxial nearest RHS 145C with adaxial base nearest RHS 158D and abaxial base nearest RHS 145D;

Inflorescence: Composite in terminal capitulum; with single row or ray florets and with disk florets in the center and 12 to 21 ray florets surrounding about 150 to 200 disk florets; to about 6 inflorescences per branch and 50 inflorescences per stem;

Flowering season: Begins in mid-July and continues for about six to seven weeks, repeating if deadheaded;

Inflorescence buds: Tubular with flat top and rounded base; with ray florets still upright about 20 mm tall and 20 mm across;

Bud color: Ray florets nearest RHS N144A;

Inflorescence longevity: Lasting about seven to ten days on the plant or as a cut flower; persistent;

Fragrance: Faint, slightly-sweet, honey-like;

Inflorescence size: To about 8 cm across and 4 cm tall;

Disk receptacle: Obconical with acute apex and flat base, about 7 mm across and 11 mm tall in maturity;

Receptacle color: Between RHS 200A and RHS 203A when flowering and nearest RHS 200A when mature;

Receptacle scale: One subtending each disk floret; linear; concavo-convex; to about 6 mm long and 1 mm across; acute apex; truncate base; entire margin; glabrous and lustrous adaxial and abaxial;

Receptacle scale color: Adaxial and abaxial distally nearest RHS N186A, proximally nearest RHS 161D, and nearest RHS 187B near middle;

Ray florets: Ligulate; sterile, neuter; about 12 to 20 ray florets in in a single whorl; sometimes imbricate; lanceolate; retuse apex with one or two notches indented about 1 mm to 2 mm; base attenuate to cuneate; margin entire;

adaxial and abaxial surface glabrous and matte; with typically two longitudinal furrowed veins; aspect horizontal with distal portion arcuate moderately downwards when mature;

*Size*.—To about 36 mm long and 8 mm across near middle.

*Ray floret color*.—Upon initially becoming flat — adaxial proximal portion between RHS 23A and RHS 21A and distal portion between RHS 17C and RHS 16A, abaxial nearest RHS 17C; near the final stage of effective inflorescence adaxial nearest RHS 17B and distally nearest RHS 13A, abaxial between RHS 17C and RHS 16A.

*Disk florets*.—Perfect; incomplete; about 350 per inflorescence arrangement in typical Fibonacci spirals; tubular with exserted anthers and style.

*Size*.—To about 8 mm long and 2 mm wide at expanded style.

*Corolla tube*.—Consisting of five tepals; to about 5 mm long and 1 mm across at apex.

*Tepals*.—Acute apex; to about 5 mm long and about 0.5 mm across at fusion; fused in basal 4 mm; margin entire; glabrous; slightly lustrous adaxial and abaxial; color apex adaxial and abaxial distally nearest RHS N186A; proximally adaxial and abaxial nearest RHS 145C and in the middle between RHS 187A and RHS 187B.

Reproductive organs: Only on disk florets;

*Gynoecium*.—To about 8 mm long; exserted.

*Style*.—Cylindrical; to about 4 mm long and 0.2 mm diameter; color nearest RHS 155C.

*Stigma*.—Bifid and reflexed in distal 1 mm; color nearest RHS N187A.

*Ovary*.—Obconical; about 3 mm long and 1 mm across at apex and about 0.5 mm diameter at base; color nearest RHS NN155B.

*Androecium*.—Connate; to about 5 mm long.

*Anthers*.—Five; synandrous; introrse; basifixed; tube to about 2.5 mm long and 0.5 mm diameter; color between RHS 202A and RHS N187A.

*Filaments*.—Five; to about 2.5 mm long and 0.1 mm diameter; color nearest RHS 4D.

*Pollen*.—Abundant; color nearest RHS 171A.

Seeds: Achene; truncate apex; acute base; surface smooth, glabrous, matte; quadrangular distally; to about 2.5 mm long and 0.7 mm across at apex; color nearest RHS N200B;

Flowering period: In Western Michigan beginning mid-July for at least six weeks; individual florets remain open for about 7 to 10 days;

Flower attitude: Upwardly;

Phyllaries: To about 27 per inflorescence in two to three whorls; aspect initially outwardly, becoming reflex downwardly with inflorescence maturity; lanceolate; acute apex; margin entire; truncate base; puberulent and matte adaxial and abaxial; to about 18 mm long and 5 mm across, decreasing proximally;

Phyllary color: Adaxial nearest RHS NN137B; abaxial between RHS 146A and RHS 137B;

Peduncles: Cylindrical; strong; stiff; upright; to about 27 cm long, 3 mm diameter proximally, and 4 mm diameter at base of inflorescence;

Peduncle color: Between RHS 146B and RHS 146A;

Growth: The new plant has been observed to have good garden performance and tolerance to high winds and strong rains.

Hardiness: Winter hardy in USDA zones 4 to 9;

Pest and disease susceptibility: Shows significant resistance to Angular Leaf Spot (*Pseudomonas* and *Xanthomonas*) and fungal leaf spot (*Septoria rudbeckiae*). Other disease resistance or susceptibility beyond that which is typical for *Rudbeckia* has not been observed.

I claim:

1. A new and distinct hardy perennial *Rudbeckia* plant named 'Treasure Trove' essentially as herein described and illustrated.

* * * * *